United States Patent
Noda et al.

(10) Patent No.: US 9,834,806 B2
(45) Date of Patent: Dec. 5, 2017

(54) MICROBE-COLLECTING CARRIER CARTRIDGE, CARRIER TREATING APPARATUS, AND METHOD OF MEASURING MICROBES

(75) Inventors: Hideyuki Noda, Kokubunji (JP); Masahiro Okanojo, Kokubunji (JP); Kenko Uchida, Tokyo (JP); Norihito Kuno, Tsurugashima (JP)

(73) Assignee: HITACHI PLANT SERVICES CO., LTD., Tokyo (JP)

( * ) Notice: Subject to any disclaimer, the term of this patent is extended or adjusted under 35 U.S.C. 154(b) by 807 days.

(21) Appl. No.: 13/001,465

(22) PCT Filed: Jun. 25, 2009

(86) PCT No.: PCT/JP2009/061587
§ 371 (c)(1),
(2), (4) Date: Mar. 30, 2011

(87) PCT Pub. No.: WO2009/157510
PCT Pub. Date: Dec. 30, 2009

(65) Prior Publication Data
US 2011/0183371 A1 Jul. 28, 2011

(30) Foreign Application Priority Data
Jun. 27, 2008 (JP) .................................. 2008-168060

(51) Int. Cl.
*C12M 1/00* (2006.01)
*C12M 1/34* (2006.01)
(Continued)

(52) U.S. Cl.
CPC .............. *C12Q 1/008* (2013.01); *B01L 3/502* (2013.01); *B01L 2300/069* (2013.01);
(Continued)

(58) Field of Classification Search
CPC ... C12Q 1/008; B01L 3/502; B01L 2300/069; B01L 2400/0487
(Continued)

(56) References Cited

U.S. PATENT DOCUMENTS 3,001,914 A * 9/1961 Andersen ......................... 435/30
3,754,868 A * 8/1973 Witz et al. ....................... 422/52
(Continued)

FOREIGN PATENT DOCUMENTS

EP 0 964 241 12/1999
EP 1 233 056 8/2002
(Continued)

OTHER PUBLICATIONS

Miyawaki et al. "Effect of water potential on sol-gel transition and intermolecular interaction of gelatin near the transition temperature", Biopolymers, 2003, 70:482-491.*
(Continued)

*Primary Examiner* — Michael L Hobbs
*Assistant Examiner* — Liban M Hassan

(57) ABSTRACT

A disposable microbe-collecting carrier cartridge and a carrier treating apparatus which efficiently convert microbes collected on a carrier into a solution and prevent variations in the amount of retrieval of microbes upon concentration on a filter are provided. A cartridge formed of an upper lid having a plurality of through holes, a container in an inverted-cone shape having both of a liquid storage sink unit having a filter at the bottom and an air suction path, and a support base for setting up a thermoplastic carrier, and a carrier treating apparatus formed of a dispensing nozzle for liquid supply, a liquid supply mechanism, a liquid heating mechanism, and a suction pump for filtration are prepared. Warm water is supplied onto the filter set up on a bottom surface of the inverted-cone-shaped. The contact with the (Continued)

warm water causes the carrier to be solated filtered through the filter.

15 Claims, 20 Drawing Sheets

(51) Int. Cl.
*C12Q 1/06* (2006.01)
*C12Q 1/00* (2006.01)
*B01L 3/00* (2006.01)
*G01N 1/22* (2006.01)

(52) U.S. Cl.
CPC .................. *B01L 2300/0681* (2013.01); *B01L 2300/1805* (2013.01); *B01L 2400/0487* (2013.01); *G01N 1/2208* (2013.01); *G01N 1/2273* (2013.01)

(58) Field of Classification Search
USPC ........................................................ 435/308.1
See application file for complete search history.

(56) References Cited

U.S. PATENT DOCUMENTS

| | | | | |
|---|---|---|---|---|
| 4,783,318 | A * | 11/1988 | Lapakko | 422/534 |
| 5,919,357 | A * | 7/1999 | Wilkins et al. | 210/120 |
| 6,391,654 | B1 | 5/2002 | Bateman | |
| 6,406,906 | B1 * | 6/2002 | Herbig et al. | 435/297.1 |
| 6,867,413 | B2 * | 3/2005 | Basch et al. | 250/255 |
| 2005/0221403 | A1 * | 10/2005 | Gazenko | 435/7.32 |
| 2006/0013726 | A1 | 1/2006 | Munenaka | |
| 2006/0121474 | A1 | 6/2006 | Kim et al. | |
| 2007/0281350 | A1 | 12/2007 | Inami et al. | |
| 2009/0286325 | A1 | 11/2009 | Tanigami et al. | |

FOREIGN PATENT DOCUMENTS

| | | |
|---|---|---|
| JP | 1132370 | 5/1989 |
| JP | 07-083831 | 3/1995 |
| JP | 7-22699 | 4/1995 |
| JP | 2000-300246 | 10/2000 |
| JP | 2000-314738 | 11/2000 |
| JP | 2001258459 | 9/2001 |
| JP | 2001-523549 A | 11/2001 |
| JP | 2002-522064 A | 7/2002 |
| JP | 2005539215 | 12/2005 |
| JP | 2006025661 | 2/2006 |
| JP | 2006094754 | 4/2006 |
| JP | 2006223207 | 8/2006 |
| JP | 2008002948 | 1/2008 |
| JP | 2008-096324 | 4/2008 |
| JP | 2008-136423 | 6/2008 |
| JP | 2009-139115 A | 6/2009 |
| JP | 2009131186 | 6/2009 |
| WO | WO 99/25465 | 5/1999 |
| WO | WO 2006/117676 | 11/2006 |

OTHER PUBLICATIONS

Hattori et al., "Rapid Measurement of Biological Contamination Using ATP-Bioluminescence Mehtod," Journal of Japan Air Cleaning Association, 2000, pp. 21-26, vol. 38, No. 5.
Noda et al., "Development of High-Sensitive Bioluminescence Detection Apparatus for Measuring Airborne Microorganisms," Proceeding of 26th Annual Technological Meeting on Air Cleaning and Contamination Control, 2008, pp. 240-242.
Murakami et al., "Application Development of Firefly Luciferase," Nippon Nogeikagaku Kaishi, 2004, pp. 630-635, vol. 78, No. 7.
JP Office Action of Appln. No. 2010-518052 dated Nov. 6, 2012.
European Search Report dated Nov. 27, 2013 in corresponding European Application No. 09770220.3.
Parks, et al., An assessment of the Sartorius MD8 microbiological air sampler, Journal of Applied Bacteriology, Blackwell Publishing Ltd., 1996, pp. 529-534, vol. 80, No. 5.
Communication pursuant to Article 94(3) EPC dated Sep. 4, 2015.

* cited by examiner

FIG. 2A
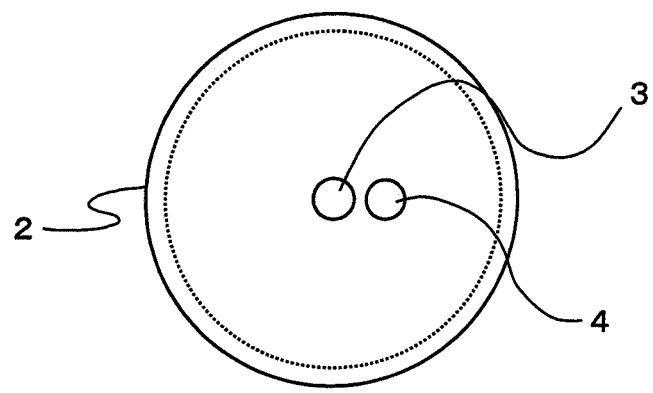
FIG. 2B
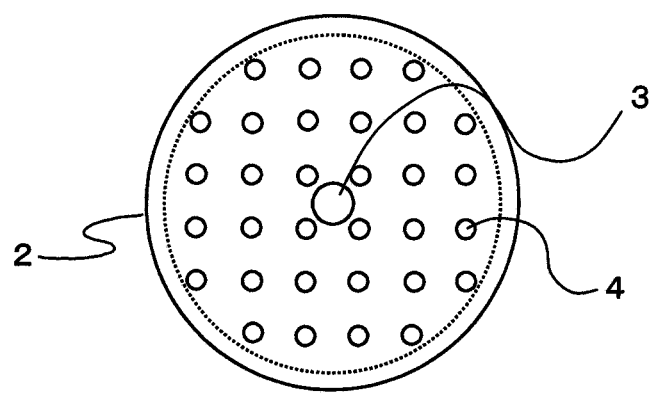
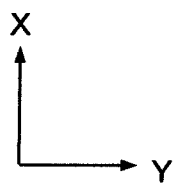

MICROBE-COLLECTING CARRIER CARTRIDGE, CARRIER TREATING APPARATUS, AND METHOD OF MEASURING MICROBES

TECHNICAL FIELD OF THE INVENTION

The present invention relates to a collection container for airborne microbes (fungi, bacteria, or microorganisms), adherent microbes, and falling microbes, and a device and a microbe counting method using this container.

BACKGROUND OF THE INVENTION

In bio-cleanrooms or on production lines of pharmaceutical and food industries, monitoring of microorganisms is required for environmental control, and thus airborne microbes, falling microbes, and adherent microbes are counted. A measuring method is defined in ISO 14698-1 by the International Organization for Standardization for bio-contamination control in cleanrooms. The cleanliness measured by the method is classified by grade. As methods of measuring airborne microorganisms, those utilizing an airborne-microbe sampler (refer to Patent Document 1) that sucks free-fall airborne microbes and a constant amount of air are generally used. In these methodologies, microbes are collected on an agar plate culture medium within a certain amount of time, and representation is made based on the number of colonies developing after cultivation. The above agar culture medium is cultured for two to seven days in an isothermal unit, and the number of colonies developed is visually counted. Then, the numbers of colonies on the culture media are averaged to obtain the number of airborne microbes. Note that, in facilities for manufacturing aseptic drugs and cell processing centers (CPCs) for producing cells where a high degree of cleanliness is required in cleanrooms, in the above-describe grade classification, the control has to be made with always maintaining Grade A or Grade B. This count for a number of particulates in the air of $\leq 3,530/m^3$ and a number of microbes of $\leq 10$ CFU (Colony Forming Unit)/$m^3$ (Grade A (inside a safety cabinet): $\leq 1$ CFU/$m^3$; and Grade B (a workplace near a safety cabinet): $\leq 10$ CFU/$m^3$).

Meanwhile, in another method (ATP method), luciferase and luciferin, which are chemiluminescence reagents, are added to ATP (adenosine triphosphate) contained in microorganisms for measuring bioluminescence. Dusts including microbes are retrieved by an airborne-microbe sampler onto an agar culture medium maintained in a dish, and are then spread to solutions or the like, thereby extracting ATP from the microbes by reagent reaction. The extracted ATP is measured by a bioluminescence method, and the amount of ATP is calculated from the obtained emission intensity. Since the amount of ATP and the number of microbes has a proportional relation, the number of airborne microbes can be calculated from the amount of ATP.

The following is a general measurement flow for airborne microbes using the ATP method.

1. Harvesting microbes by an airborne-microbe sampler;
2. Retrieving gathered microbes and spreading them to solutions or the like;
3. Eliminating dead microbes in a microbe liquid and eliminating exogenous ATP not derived from microbes;
4. Extracting ATP in viable microbes; and
5. Bioluminescence, measurement, and counting by adding a chemiluminescence reagent.

Regarding the above measurement flow 1, an impactor-type sampler in a porous nozzle form is used, and dusts included in 1 $m^3$ of air are retrieved for 10 to 20 minutes onto a plate culture medium in a petri dish (refer to Non-Patent Document 1). The ratio of retrieving microbes is equal to or greater than 90%. In cleanrooms and safety cabinets with a high degree of cleanliness, several microbes are gathered by taking time of about 20 minutes.

Regarding the above measurement flow 2, the microbes gathered onto the plate culture medium through collection are peeled off from the surface, and are retrieved into a separately-prepared container as a liquid sample. To totally retrieve microbes, retrieval of the microbes captured on the culture medium has to be reliably performed, and the skills of the operator and selection of a solution are important. Also, here, if the tool for retrieval itself is contaminated, correct counting cannot be performed.

Regarding the above measurement flows 3 and 4, along with an advance of development of reagents (refer to Non-Patent Document 3), it has become possible to easily eliminate dead microbes and exogenous ATP and extract ATP in microbes. An ATP eliminating reagent containing apyrase and adenosine phosphate deaminase as principal components is added to a liquid sample to be measured for reaction for 30 minutes, and then an ATP extraction reagent containing a surface-active agent as a principal component is added for reaction for 30 to 60 seconds. In this manner, a preparation for measuring only ATP derived from viable microbes is ready.

Regarding the above measurement flow 5, biochemical emission by adding a chemiluminescence reagent to the extracted liquid after ATP derived from viable microbes is extracted or by retrieving the extracted liquid after ATP derived from viable microbes is extracted and adding and mixing the extracted liquid with a chemiluminescence reagent is detected by a photodetector. Since the number of microbes is proportional to the amount of ATP, the number of microbes is calculated from the amount of ATP chemiluminescence.

In an ATP chemiluminescence assay, to measure ATP chemiluminescence at a high degree of sensitivity and a high accuracy, it is important to use a highly-sensitive detector and achieving a high degree of light gathering with an optical arrangement of the detector and a chemiluminescence reaction field. Furthermore, it is important to achieve a light-shielding mechanism for suppressing the entrance of stray light as much as possible because the accuracy of chemiluminescence measurement is decreased when light coming from the outside of the apparatus or coming from things other than the chemiluminescent substance, which is called stray light, enters the inside of the apparatus. According to FIG. 2 of Non-Patent Document 1 (paper), a lower limit of detecting ATP is $1 \times 10^{-17}$ mol (10 amol), which corresponds to a degree of sensitivity on the order of ten microbes in terms of the number of microbes. When airborne microbes are taken as a target, a detection sensitivity allowing one microbe to be detected is required. Therefore, in Non-Patent Document 1, cultivation at 35° C. for six hours is often inserted between the above measurement flows 1 and 2 (FIG. 9 of Non-Patent Document 1 (paper)).

In recent years, the amount of ATP can be measured from 1 amol with a bioluminescence detection system in which a dispenser and a detector are placed in a light-shielded space in a same device (FIG. 3 of Non-Patent Document 2 (paper)).

As to highly sensitive detectors, conventionally, a photomultiplier is used as a photodetector of a microorganism counting device including a luminometer for ATP measurement or a luminometer using ATP chemiluminescence. When using more highly sensitive detectors, photocounting is adopted in which a signal of the photomultiplier is subjected to digital processing. Next, as to an optical arrangement, since light intensity is attenuated by the square of a distance from a chemiluminescence-emitting point, it is said to be preferable to make a sample container containing chemiluminescent substance closer to a light-receiving surface. Also, since light from the chemiluminescence-emitting point is scattered in a spherical form, an optical arrangement for efficient retrieval onto the light-receiving surface is important. Note that, while light retrieval efficiency is often defined with a solid angle, in this manner, in order to achieve a higher sensitivity, it is important to make the light-receiving surface closer to the container and to prepare a large light-receiving surface with respect to a light-emitting area. It is also effective to surround a container holder with a mirror-surface member so as to forcefully reflect light from a mirror surface and to guide the light to the light-receiving surface.

Note that the order of the measurement flows 2, 3, and 4 is random. In an embodiment, the flows 3 and 4 are performed first, and then an ATP-extracted microbe liquid is retrieved in the flow 2.

Also, if falling microbes and adherent microbes are collected by a dedicated carrier in the measurement flow 1, the falling microbes and the adherent microbes can be measured in the same process from the measurement flow 2 onward.

Patent Documents
Patent Document 1: Japanese Patent Application Laid-Open Publication No. 2000-300246
Patent Document 2: Japanese Patent Application Laid-Open Publication No. 2000-314738
Patent Document 3: Japanese Patent Application Laid-Open Publication No. 7-83831
Non-Patent Documents
Non-Patent Document 1: Journal of Japan Air Cleaning Association, Vol. 38, No. 5, pp. 21-26, 2000
Non-Patent Document 2: Proceeding of 26th Annual Technological Meeting on Air Cleaning and Contamination Control, pp. 240-242, 2008
Non-Patent Document 3: Nippon Nogeikagaku Kaishi Vol. 78, No. 7, pp. 630-635, 2004

SUMMARY OF THE INVENTION

Problems to be Solved by the Invention

As the sensitivity of chemiluminescence detecting devices has increased, 1 amol of the amount of ATP has become measureable, and thus, if several microbes are present, they can be detected in principle. However, retrieval of the gathered microbes and spread to a solution or the like are performed with a manual operation under present circumstances, and the operators have to acquire skills to totally retrieve microbes, and moreover, if the tool for retrieval itself is contaminated, reliability and reproducibility of the results are lost. Although there is a method in which a measurement is performed after the number of microbes is grew on the order of tenfold by a short-time cultivation, the grow rate changes depending on the type of microbes and nutritional conditions of the culture medium, and therefore accurate counting is difficult. In terms of industrial value, unlike conventional cultivation methods, if an ATP method without requiring cultivation and capable of checking cleanliness within one hour can be used in a bio-cleanroom cleanliness monitor, the product shipping efficiency can be significantly improved, and plant facilities for stocking products are not required, and thus same-day shipping can be achieved.

The present invention has been made in view of the above circumstances, and the present invention provides a configuration of a microbe-collecting carrier container and a carrier treating apparatus capable of spreading gathered microbes full-automatically to solutions and the like at a high retrieval ratio. In particular, the present invention provides a device and an apparatus capable of detecting at least one microbe in a microbe counting method by an ATP method without requiring cultivation.

Means for Solving the Problems

To solve the above problems, an upper lid having a plurality of through holes, a container having a liquid storage sink unit having a filter at the bottom together with an air suction path, and a support base for setting up a thermoplastic carrier, such as gelatin are prepared. The upper lid, the container, and the support base are integrally formed, and the support base is configured to be inserted between the container and the upper lid. The support base is arranged so as not to make contact with the upper lid or the filter at the bottom of the container, and is set up in the liquid storage sink unit inside the container. A housing for these components is hereinafter described as a microbe-collecting carrier cartridge.

The plurality of through holes of the upper lid of the microbe-collecting carrier cartridge are used for an impactor nozzle, which is means of letting airborne microbes pass through with air to collect the airborne microbes and as dispensing nozzle introduction holes for liquid supply for supplying a liquid to the liquid storage sink. On the support base, a thermoplastic carrier causing a sol-gel phase transition in a temperature depending manner is set up. Here, for example, a carrier having a transition temperature at 37° C. is prepared.

A collector that sucks gas with a suction fan is separately prepared, and the collecting carrier cartridge is set up at a head of the collector. Air is inhaled through the suction path of the container unit of the collecting carrier cartridge, and dusts including microbes in the air are harvested on a surface of the carrier in a gel form with the principle of the impactor.

After the dust collection is ended, the cartridge is removed from the collector and is set up in a carrier treating apparatus. The carrier treating apparatus is configured of a dispensing nozzle for liquid supply, a liquid supply mechanism, a liquid heating mechanism, and a suction pump for filtration. The dispensing nozzle for liquid supply is inserted in the dispersing nozzle introduction hole for liquid supply of the upper lid to supply warm water (≥37° C.) onto the filter. Upon liquid supply, the suction pump for filtration is stopped. Warm water to be supplied onto the filter is stored with time in the liquid storage sink. With warm water in contact with the carrier in which a sol-gel phase transition occurs at 37° C., the carrier in a gel form is changed to a sol state, and the solated carrier is mixed with the warm water and can be handled as a liquid. After the carrier is solated and mixed and diluted with the warm water, the suction pump of the filtration apparatus is driven for suction and filtration of the mixed liquid via the filter of the collecting carrier cartridge. By using the filter having a shape not allowing microbes to pass through but having a gap, only microbes are captured on the filter after the suction and filtration. Polymers and dusts to be a background in a chemiluminescence reaction pass through the filter by filtration, and are excluded by the suction pump.

Next, an ATP extraction liquid is added onto the filter, and ATP molecules are extracted from the inside of the microbes captured on the filter through filtration. After the extraction, a dedicated chemiluminescence measuring device and a chemiluminescence reagent of luciferin and luciferase are prepared, and the ATP extraction liquid after an ATP extraction reaction is finished and the chemiluminescent reagent are mixed together. By the chemiluminescence measuring device, the amount of chemiluminescence is measured. From the obtained chemiluminescence intensity, the amount of ATP is calculated and, furthermore, based on the amount of ATP, a number of microbes is calculated for counting.

Further features of the present invention will become apparent by the following best modes for carrying out the invention and attached drawings.

Effects of the Invention

The cartridge according to the present invention has first an effect of achieving a collecting capability equivalent to that of the collecting carrier in the conventional technology by harvesting the airborne microbes, falling microbes, and adherent microbes by a carrier in a gel form. Second, since the collecting carrier can be subjected to a phase transition to a sol form and the collecting carrier is diluted as it is and thus can be handled as a liquid mixed with warm water, and so the collecting carrier becomes a microbe suspension at this process and a process of extracting by peeling off from the solid surface, that is, the culture medium using a liquid is not required. With the solation, 100% of microbes can be retrieved in the liquid and, by filtration of liquid components, an extremely high retrieval ratio can be effectively achieved. Also, a complicated extracting process can be replaced by a simple process of adding a warmed liquid, thereby achieving effects of automation, simplification of system configuration, speedy process, improvement in reproducibility, reduction in contamination risks, and others.

Since the cell suspension according to the present invention has a small amount of liquid, a concentration of microbes is high, and a use efficiency of microbes is also high. Also, by filtration or the like of the cell suspension to capture microbes in the cell suspension onto the filter, an effect can be achieved such that the liquid amount can be substantially zero and the concentration and use efficiency of microbes are dramatically increased. Furthermore, influences of the water-soluble property or small-particle-diameter contaminants can be effectively eliminated to achieve a high reliability. That is, there is an advantage in which a measurement of microbes can be automatically performed with high sensitivity and high accuracy.

Therefore, the present invention has an effect of achieving high measurement accuracy and sensitivity, and obtaining easy-and-quick results in inspections of airborne microbes, adherent microbes, and falling microbes.

BRIEF DESCRIPTIONS OF THE DRAWINGS

FIG. 2A is a diagram (1) illustrating a structure of an upper lid according to the first embodiment;

FIG. 2B is a diagram (2) illustrating a structure of the upper lid according to the first embodiment;

Figure 14A:
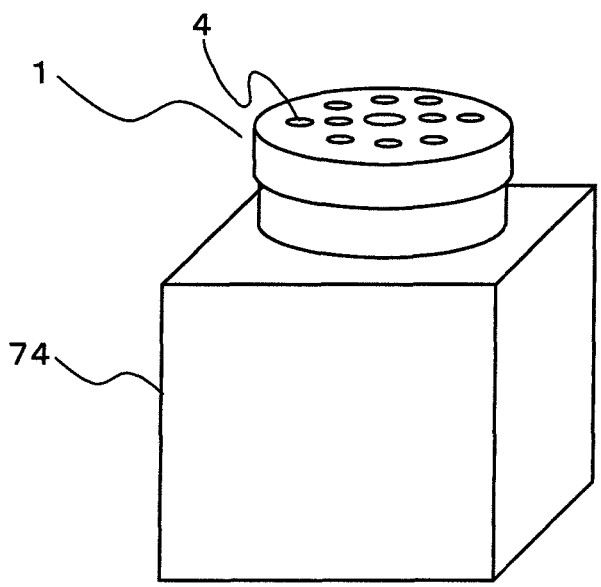
Figure 14B:
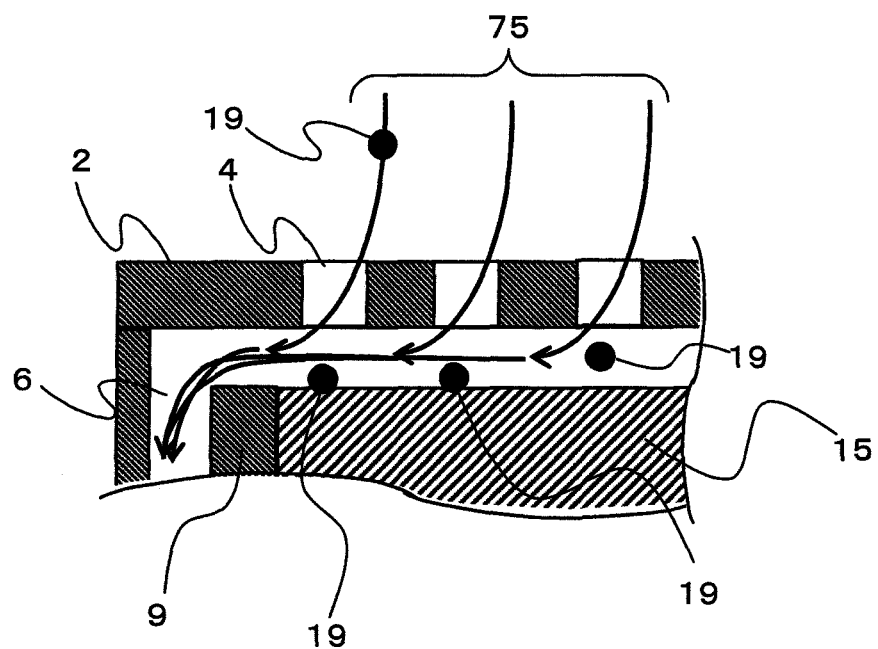

FIG. 14A is a schematic diagram (1) illustrating a state in which a collection carrier cartridge according to the second embodiment is set up in a collector and illustrating a principle of an impactor; and FIG. 14B is a schematic diagram (2) illustrating a state in which the collection carrier cartridge according to the second embodiment is setup in the collector and illustrating the principle of the impactor.

DESCRIPTIONS OF THE PREFERRED EMBODIMENTS

In the following, embodiments of the present invention will be described with reference to the accompanying drawings. However, it should be noted that these embodiments are merely examples for achieving the present invention and are not meant to restrict the present invention. Also, components which are common among the drawings are denoted by the same reference numerals.

First Embodiment

Figure 1A:
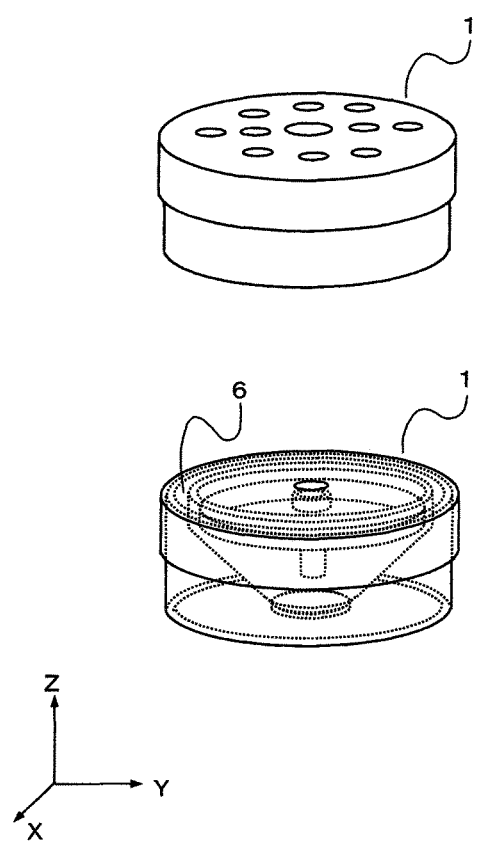
FIG. 1A is a diagram (1) illustrating a configuration of a microbe-collecting carrier cartridge according to a first embodiment.
Figure 1B:
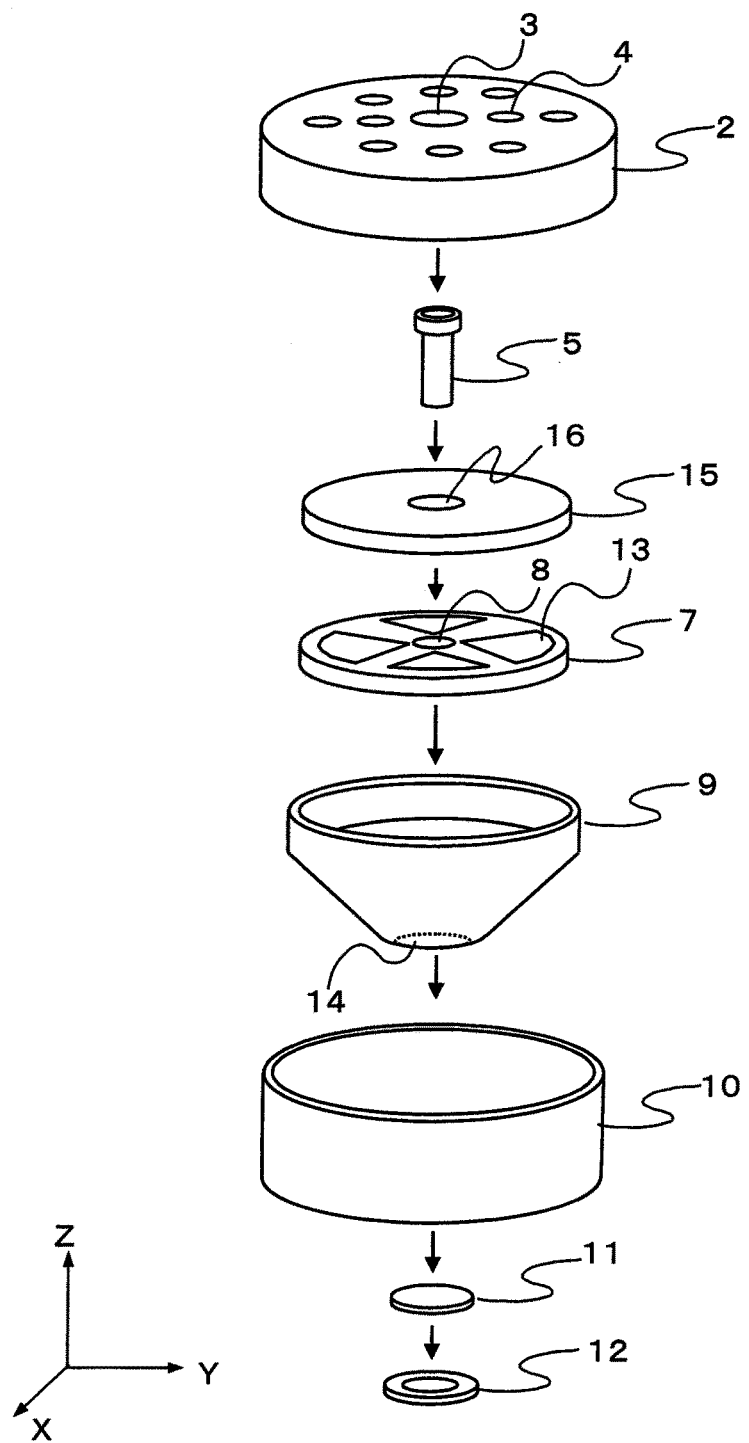
FIG. 1B is a diagram (2) illustrating a configuration of the microbe-collecting carrier cartridge according to the first embodiment.

FIGS. 1A and 1B are diagrams illustrating a schematic configuration of a microbe-collecting carrier cartridge according to a first embodiment. FIG. 1A is a completed assembly diagram and its see-through diagram of a microbe-collecting carrier cartridge 1 of the present invention. FIG. 1B illustrates a schematic configuration in a form of an exploded view to facilitate the description. The microbe-collecting carrier cartridge 1 is formed of an upper lid 2, a dispensing nozzle guide 5, a thermoplastic carrier 15, a carrier support base 7, a liquid storage container 9, and an outer cylinder 10.

In the upper lid 2, a first through hole 3 positioned on the same center axis as that of the dispensing nozzle guide 5 and second through holes 4 for impactor nozzles are formed along a z axis.

The dispensing nozzle guide 5 is inserted in a third through hole 8 in the carrier support base 7, and has a structure of being hung and fixed at an upper portion of an umbrella structure of itself. Here, the dispensing nozzle guide 5 may be integrally molded with the carrier support base 7.

The thermoplastic carrier 15, which has through-hole 16 and which harvests microbes, is set up on the carrier support base 7, is set up so as to cover the umbrella portion of the dispensing nozzle guide 5, and has a fifth through hole 14. The second through holes 4 are, having the carrier support base 7 and the dispensing nozzle guide 5 being assembled, to put thermoplastic polymer heated to be in a solated state on the carrier support base 7 and lower the temperature of the thermoplastic polymer to a temperature near the room temperature for gelating and solidifying the thermoplastic polymer. The second through holes 4 are formed upon gelating and solidifying on the carrier support base 7. As a matter of course, the thermoplastic carrier 15 may be formed in a donut shape by die cutting and then fit into the carrier support base 7.

The carrier support base 7 is formed of not only the third through hole 8 for insertion of the dispensing nozzle guide 5 at the center but also a plurality of fourth through holes 13 on a flat plate. The liquid storage container 9 is a cup having an inverted-cone shape or a trumpet shape. Its bottom surface is in an open form, and a microbe collection filter 11 is set up at its fifth through hole 14, the microbe collection filter 11 being fixed at the bottom of the liquid storage container 9 with a donut-shaped holding plate 12. Since the outer cylinder 10 has a diameter larger than that of the liquid storage container 9, as depicted in FIG. 1A, after the microbe-collecting carrier cartridge 1 is assembled, a gap 6 is formed between the outer cylinder 10 and the liquid storage container 9. For the sake of description, the liquid storage container 9 and the outer cylinder 10 are shown as disassembled (FIG. 1B), but the liquid storage container 9 and the outer cylinder 10 are preferably coupled together with bridges routed at several points. The gap 6 is used as an air intake for inflow of air into the second through holes 4 for impactor nozzles.

The material of each part is preferably autoclavable in view of sterilization before use, and polypropylene, polyether-ketone-ketone (PEEK), which are resin materials having a high melting point, are suitable and, as for metal, stainless and the like are suitable. In view of disposability, polypropylene and PEEK material are suitable.

A manufacturing method may be taken in which the upper lid 2, the dispensing nozzle guide 5, the support base 7, the liquid storage container 9, and the outer cylinder 10 are separately manufactured and then each member is manually mounted, meanwhile, it is preferable that manufacturing is done by integral molding as much as possible using injection molding.

FIGS. 2A and 2B are schematic diagrams of the upper lid 2 viewed from an x-y plane. There is a single second through hole 4 for an impactor nozzle in FIG. 2A, and there are a plurality of the second through holes 4 in FIG. 2B. When a portable-type collector that can be carried is used, the capacity of a suction fan of the collector is small, and therefore, in view of a flow-path resistance, the flow velocity of each impactor nozzle can be more increased when the porous type of FIG. 2B is used, and the collection efficiency of airborne microbes can be increased. In general, the number of holes is 100 to 600, the hole diameter is equal to or smaller than 0.6 mm, and the holes are arranged with a space of several mm. When a collector of a setting type without a size limit is used, the capacity of the suction fan can be large, and therefore the upper lid 2 with a single-type impactor nozzle of FIG. 2A is preferable to use. An advantage of the single-type impactor nozzle is that microbes can be collected in a narrow area, and therefore the microbe-collecting carrier cartridge 1 can be designed and manufactured to be small. For example, when the upper lid of FIG. 2A is used, the outer diameter dimension of the microbe-collecting carrier cartridge 1 may be on the order of 10 mm, however, when the upper lid of FIG. 2B is used, since holes as many as described above are arranged, the outer diameter dimension is required to be on the order of 40 mm at minimum.

Figure 3A:
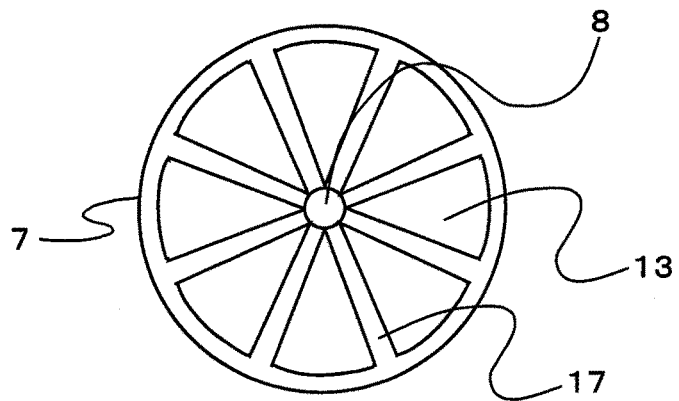
FIG. 3A is a diagram (1) illustrating a structure of a carrier support base according to the first embodiment.
Figure 3B:
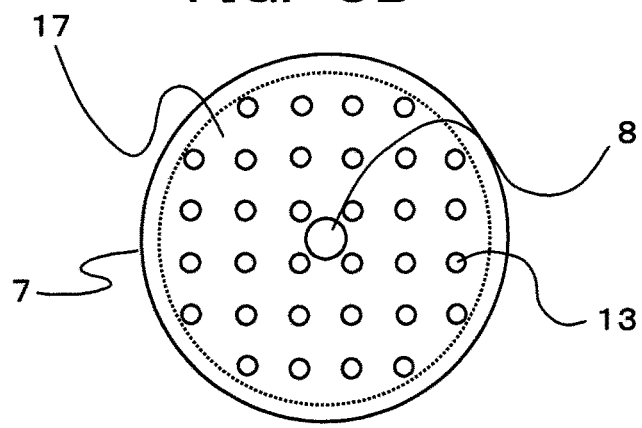
FIG. 3B is a diagram (2) illustrating a structure of the carrier support base according to the first embodiment.
Figure 3C:
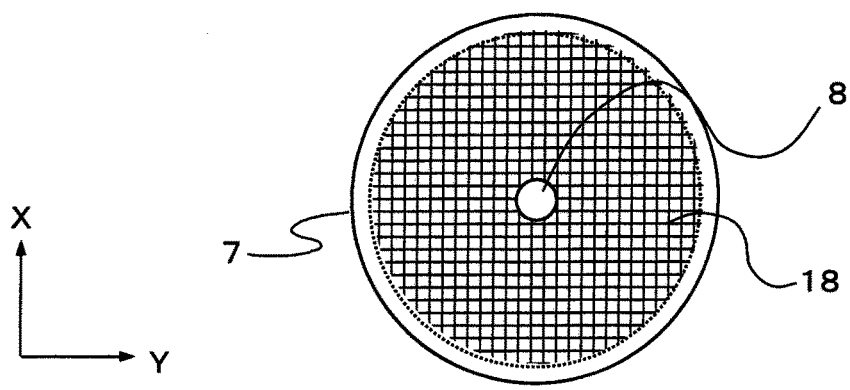
FIG. 3C is a diagram (3) illustrating a structure of the carrier support base according to the first embodiment.

FIGS. 3A to 3C are schematic diagrams of the carrier support base 7 viewed from an x-y plane. In FIG. 3A, a plurality of fourth through holes 13 each in a fan shape are radially formed, centered at the third through hole 8. In FIG. 3B, a plurality of circular fourth through holes 13 are formed at regular spacings, centered at the third through hole 8. FIG. 3C depicts a carrier support base 7 using a mesh 18.

On the carrier support base 7, the thermoplastic carrier 15 is set up. Depending on the hardness of the thermoplastic carrier 15, any one of the forms shown in FIGS. 3A, 3B, and 3C is preferably used. As the thermoplastic carrier 15 is harder in a gel state, the area of a support portion 17 of the carrier support base 7 may be smaller. In that case, the carrier support base 7 of FIG. 3A may be preferably used. While a liquefied carrier polymer passes through the fourth through hole to fall into the liquid storage container 9 when the thermoplastic polymer is solated, the smaller the area of the region of the support portion 17, the less the amount of liquid supposed to remain on the support portion 17. In other words, the smaller the area of the region of the support portion is, the more efficiently the microbes captured on the thermoplastic carrier 15 can be collected in the liquid storage container 9.

FIG. 3C depicts one aspect capable of supporting the thermoplastic carrier 15 on the carrier support base 7 even if the thermoplastic carrier 15 is relatively soft in a gel state. Since the area of the support portion is small, the amount of liquid remaining on the support portion 17 of the carrier support base 7 can be reduced.

By using the one depicted in FIG. 3B, the thermoplastic carrier 15 can be most stably supported, but the residual amount of liquid on the carrier support base 7 is disadvantageously increased. As a method of reducing the residual amount of liquid, the surface of the carrier support base 7 may be made water-repellent.

Figure 4:
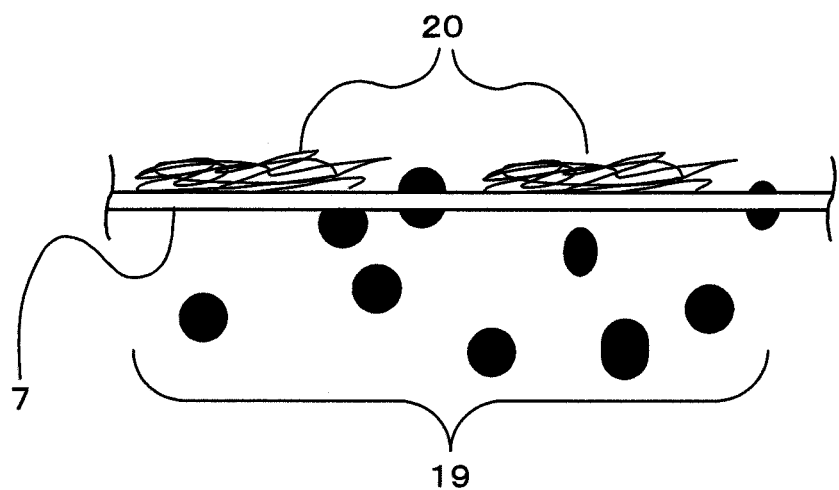
FIG. 4 is a schematic diagram in which a carrier support base 7 according to the first embodiment is used as a pre-filter.
Figure 5A:
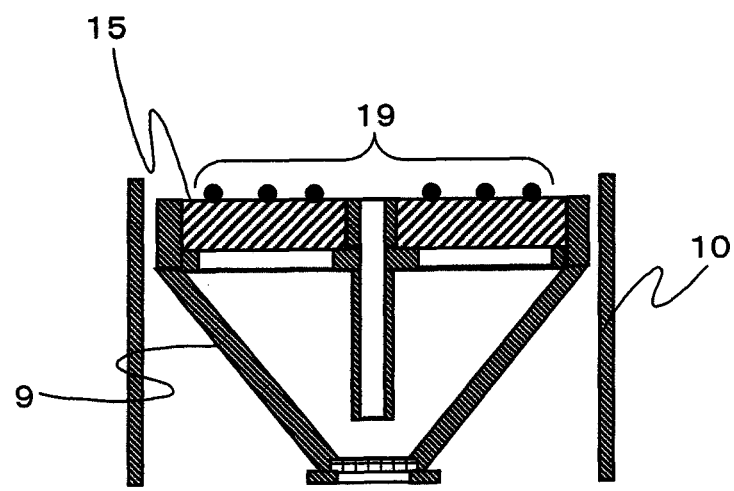
FIG. 5A is a schematic diagram (1) illustrating a state in which microbes on a thermoplastic carrier according to the first embodiment are harvested on a microbe collection filter.
Figure 5B:
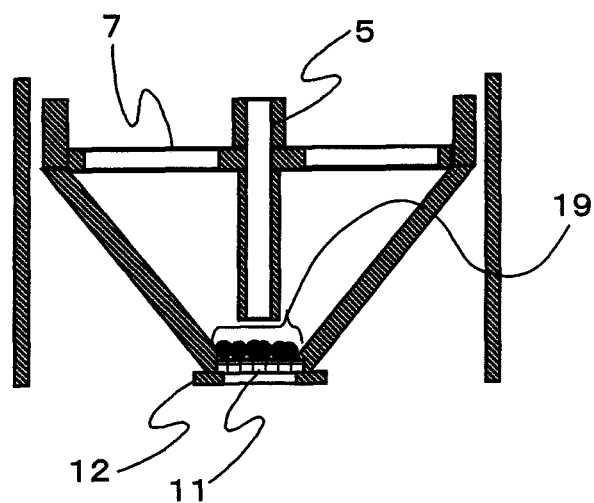
FIG. 5B is a schematic diagram (2) illustrating a state in which microbes on the thermoplastic carrier according to the first embodiment are harvested on the microbe collection filter.

Other than the function of supporting the thermoplastic carrier 15, as an addition of another function, there is an aspect of using the carrier support base 7 as a pre-filter for trapping dust other than microbes 19 (FIG. 4). On the thermoplastic carrier 15, in addition to the microbes 19, dust 20 is present. In view of the size of a cell body, the carrier support base 7 formed with the fourth through holes 13 each being larger than, for example, 1 micron, or each having a size about ten times larger than that is used.

The thermoplastic carrier 15 is a polymer that makes a transition from a gel to a sol state when heated at 30° C. and higher and completely liquefies at 37 to 40° C., and, for example, any of gelatin, a mixture of gelatin and glycerol, and, furthermore, a copolymer having a ratio between N-acryloylglycineamide and N-methacroyl-N'-biotinylpropylenediamine (MBPDA) being 10:1 or others is used.

When the thermoplastic carrier 15 is heated at a temperature equal to or higher than 30° C., for example, 37° C., and a solated polymer liquid is subjected to suction and filtration, as depicted in FIGS. 5A and 5B, microbes are harvested from a top of the thermoplastic carrier 15 to a top of the microbe collection filter 11. While a method of solating the thermoplastic carrier 15 will be described in a second embodiment using a carrier treating apparatus of FIG. 6, with the inverted-cone shape or trumpet shape of the liquid storage container 9, the microbes 19 are collected in a narrow region on the microbe collection filter 11 for further concentration. Here, in an environment of the concentrated microbes 19, the amount of liquid is ideally zero, and the concentration of the microbes can be freely controlled by controlling the amount of liquid to be added next. When the diameter of an effective surface of the microbe collection filter 11 is on the order of several mm to 10 mm, a liquid is added at a level of several microliters to 100 microliters to prepare a microbe suspension in the liquid storage container 9. In terms of results, the concentration of the microbes 19 when 1 $mm^3$ (1000 liters) of air is collected by a collector is concentrated ten thousand times to hundred thousand times on the microbe collection filter 11.

The microbe collection filter 11 may be made of any material as long as it lets a solution pass but does not let microbes pass therethrough, and may be in either of a HEPA (High Efficiency Particulate Air) shape and a pore shape. For example, in consideration of the size of microbes, the material may be any as long as it does not allow passage of a substance equal to or larger than 0.45 microns.

Second Embodiment

FIG. 6 is a diagram illustrating a schematic configuration of a carrier treating apparatus according to a second embodiment. The carrier treating apparatus is formed of a liquid supply unit, a temperature control unit, and a filtration control unit, dissolving the thermoplastic carrier 15 in the microbe-collecting carrier cartridge 1 for filtration and suction to harvest on the microbe collection filter 11. The process of the apparatus as a whole is continuously and automatically controlled by using a first control device 35.

In FIG. 6, the microbe-collecting carrier cartridge 1 is set on a first plate member 21. The plate of the plate member 21 at a place for setting the microbe-collecting carrier cartridge 1 is penetrated so as to allow a microbe-solution suction nozzle 31 to make contact with a bottom surface of the microbe-collecting carrier cartridge 1 via the first plate member 21.

First, the liquid supply unit and the temperature control unit will be described.

Along a z axis at the center of the first through hole 3, a first dispensing nozzle 22 is positioned above the microbe-collecting carrier cartridge 1, and the first dispensing nozzle 22 is fixed to a first nozzle holder 23 and, furthermore, the first nozzle holder 23 is fixed to a first actuator 26. With a shift of the first actuator 26, the first dispensing nozzle 22 can be introduced into the first through hole 3 of the microbe-collecting carrier cartridge 1, passing through inside the dispensing nozzle guide 5 to come closer immediately above the microbe collection filter 11. The first dispensing nozzle 22 is connected to a first pipe 24, a second pipe 26, and a third pipe 28, and the third liquid pipe 28 is accommodated in a first solution tank 29 via a pipe heating heater 25 and a first liquid-delivering pump 27. The first solution tank 29 is set up on a solution tank heater 30. Although it has been described that three pipes are interposed between the first dispensing nozzle 22 and the first solution tank 29, the number of pipes may be one. In this case, a peristaltic-type or diaphragm-type pump is preferably used as the first liquid-delivering pump 27. Note that, other than that, the first liquid-delivering pump 27 may be a syringe pump using a syringe. As the pipe heating heater 25, a far-infrared ceramic heater, a sheathed heater, a silicon rubber heater, or the like is used. When a far-infrared ceramic heater is used, it is preferable that a pipe in a coil shape is inserted in the heater for heating a long pipe distance. This is because, if the pipe length is short, while the liquid moves in a liquid delivering process, the solution moves to the first pipe 24 without being heated to a set temperature. When a sheathed heater is used, a pipe is wound around a heater surface in a spiral shape a plurality of times to heat a long pipe distance. When a silicon rubber heater is used, a heater is preferably wound around a pipe for a long distance to heat a long pipe distance. Whenever any of these heaters is selected, the pipe heating heater 25 is preferably covered with a heat insulating material to suppress dissipation of an amount of heat to the outside. As the solution tank heater 30, a plate resistance-heating type, Peltier element type, or the like is used. The temperatures of the pipe heating heater 25 and the solution tank heater 30 are monitored by a temperature measurement device, such as a thermocouple element, to keep the temperature constant.

Next, the filtration control unit will be described.

The microbe-solution suction nozzle 31 is present below and along the z axis at the center of the microbe collection filter 11 of the microbe-collecting carrier cartridge 1, and is fixed to a second actuator 32. With a shift of the second actuator 32, the microbe-solution suction nozzle 31 makes contact with the donut-shaped holding plate 12 for fixing the microbe collection filter 11 of the microbe-collecting carrier cartridge 1. At the tip of the microbe-solution suction nozzle 31, an O-ring rubber 36 is mounted to make close contact when making contact with the donut-shaped holding plate 12 to achieve a leak-less connection with the microbe collection filter 11. The microbe-solution suction nozzle 31 is connected to a suction pump 34, such as an aspirator, via a fourth pipe 33. ON/OFF control of the suction pump 34 and up-and-down shift of the second actuator 32 are controlled by the first control device 35.

Figure 6:
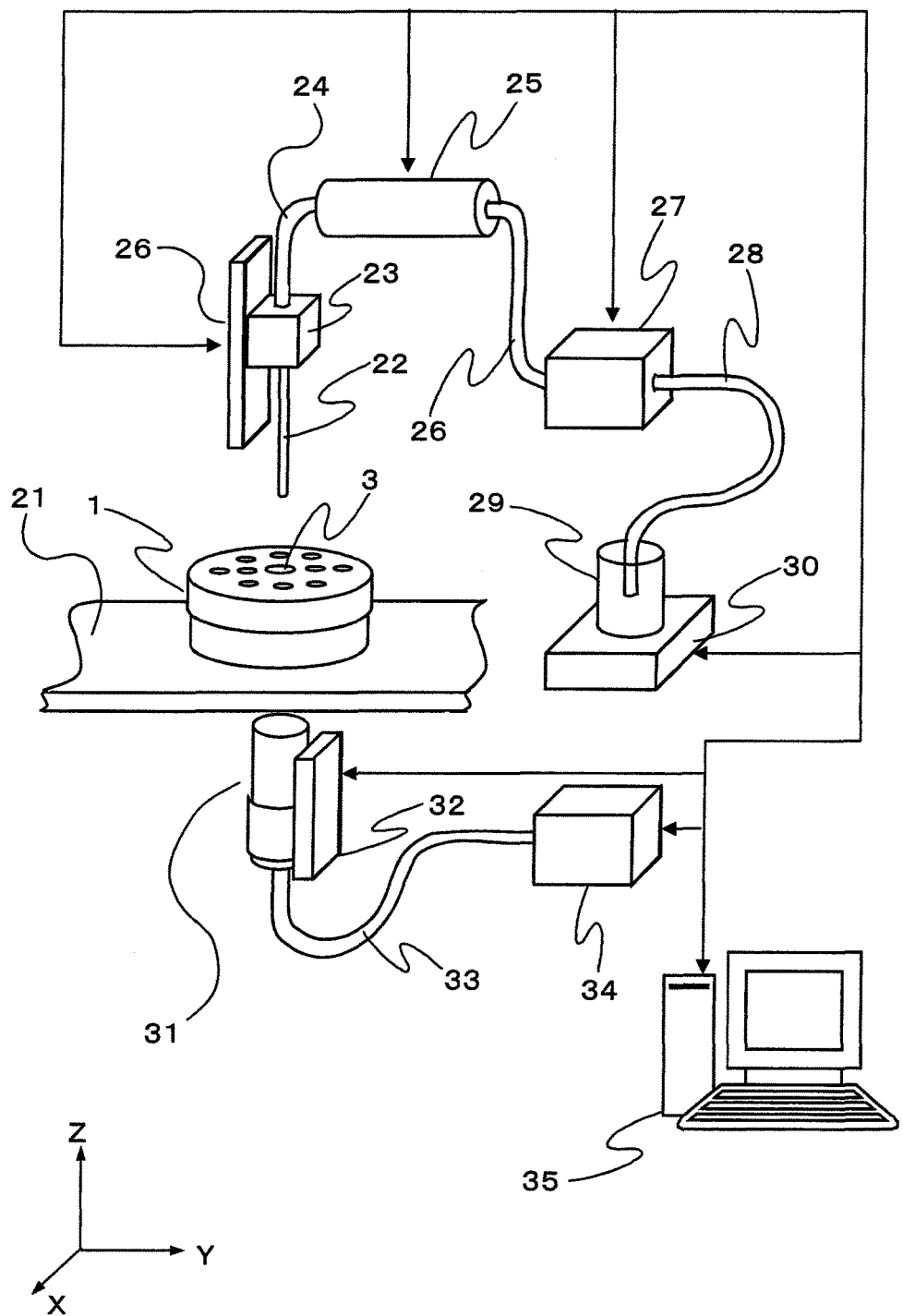
FIG. 6 is a diagram illustrating an outer appearance of a carrier treating apparatus according to a second embodiment.

FIGS. 7A to 7F are diagrams for describing a principle of operation of the carrier treating apparatus (FIG. 6) according to the second embodiment. The microbe collecting process using a collector has been already done, and the microbes 19 are captured on the thermoplastic carrier 15. A process of setting up the microbe-collecting carrier cartridge 1 on the treating device of FIG. 6 and harvesting on the microbe-collecting filter 11 will be described. Note that the drawings are illustrated having the upper lid 2 omitted for simplification. The thermoplastic carrier 15 for use here is gelatin, which is solated, that is, changed from a solid to a liquid, at 37° C.

Figure 7A:
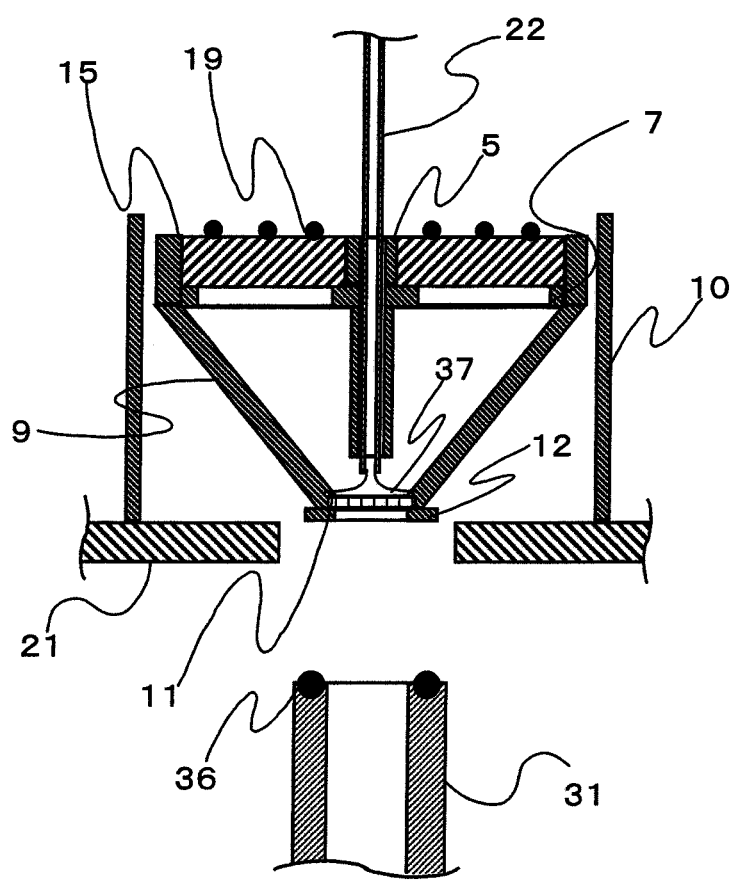
FIG. 7A is a diagram (1) illustrating a principle of operation of the carrier treating apparatus according to the second embodiment.

FIG. 7A illustrates a state in which, in response to an instruction of starting a process given from the first control device 35, the first actuator 26 is activated, and the first dispensing nozzle 22 passes through the dispensing nozzle guide 5 of the microbe-collecting carrier cartridge 1 to come closer to the microbe collection filter 11 in the liquid storage container 9. Further, the drawing illustrates a condition immediately after a heated solution 37 supplied from the first solution tank 29 is dispensed from the first dispensing nozzle 22. As the heated solution 37, a phosphate buffer or sterile water is suitably used. Here, a phosphate buffer at 40° C. was used. Meanwhile, the temperature of 40° C. is a result of a preliminary measurement in the liquid storage container 9. The temperature is an average temperature measured in the storage container 9 when the set temperature of the pipe heating heater 25 at the previous stage is set at 80° C. and a liquid with fluctuations in range of 45 to 50° C. at a flow velocity of 1 mL/min is supplied from the first dispensing nozzle 22 into the liquid storage container 9. Also, here, only the pipe heating heater 25 is used for heating a solution, but a combined use of the pipe heating heater 25 and the solution tank heater 30 or a single use of the solution tank heater 30 may be taken.

Figure 7B:
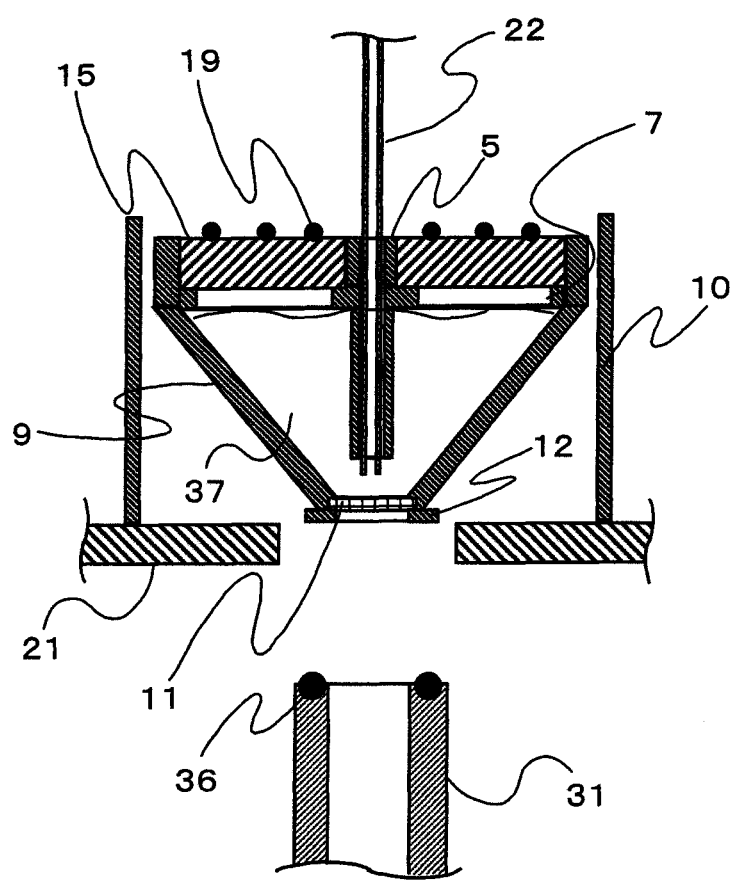
FIG. 7B is a diagram (2) illustrating the principle of operation of the carrier treating apparatus according to the second embodiment.

FIG. 7B illustrates a state five minutes after dispensing starts. An inner capacity of a portion between the microbe collection filter 11 of the liquid storage container 9 and the carrier support base 7 is 5 mL, and the state of FIG. 7B is just at the timing of the thermoplastic carrier 15 has only started making contact with the heated solution 37.

Figure 7C:
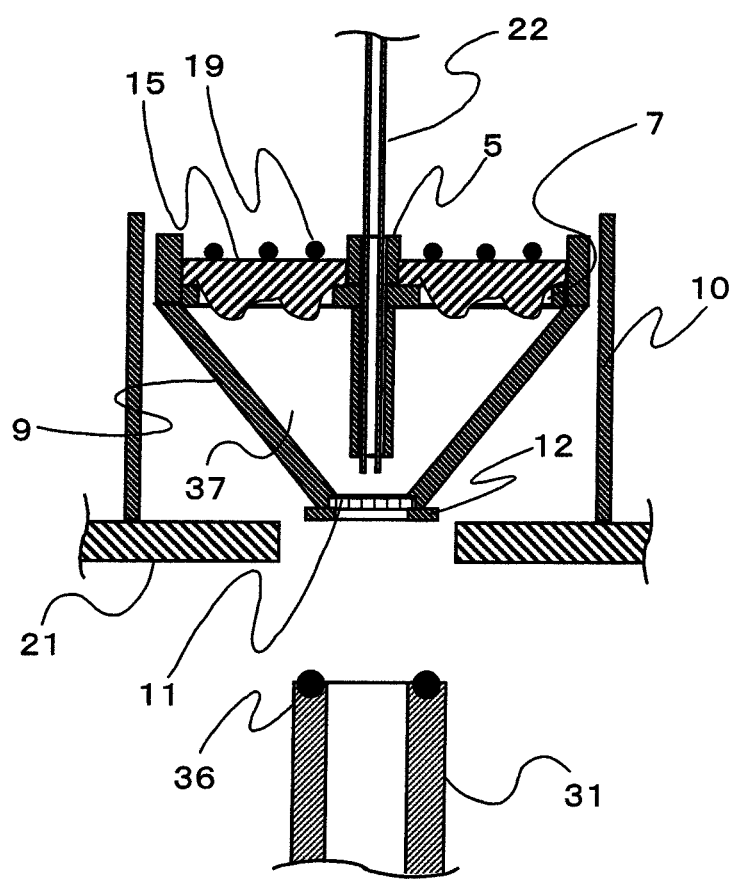
FIG. 7C is a diagram (3) illustrating the principle of operation of the carrier treating apparatus according to the second embodiment.
Figure 7D:
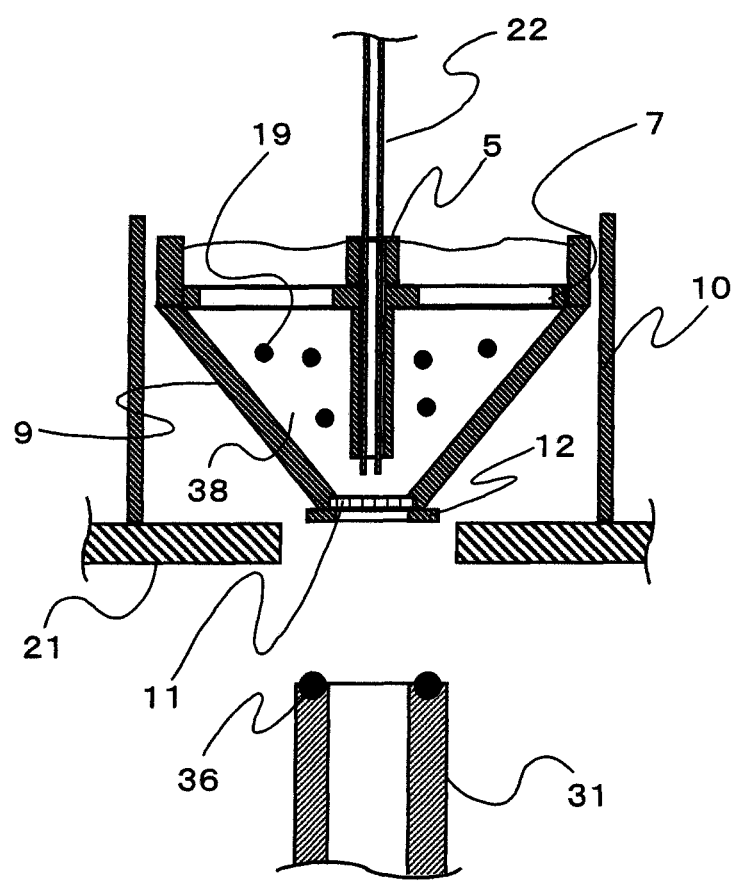
FIG. 7D is a diagram (4) illustrating the principle of operation of the carrier treating apparatus according to the second embodiment.

FIG. 7C illustrates a condition in which the dispensing is further continued to cause approximately 7 mL of the heated solution 37 to be supplied into the liquid storage container 9 and then further the supply is being stopped. Furthermore, FIG. 7C illustrates an initial liquefied condition in which a polymer of the thermoplastic carrier makes a sol transfer. In FIG. 7D, after several minutes, the polymer of the thermoplastic carrier is completely liquefied and a mixed liquid 38 of the heated liquid and the polymer is just formed. The microbes 19 suspend to form a microbe suspension.

In FIGS. 7A to D, while the thermoplastic carrier is caused to make a sol transition with the heated solution from the dispensing nozzle, a sol transition may be made by heating the carrier support or the like. Also, dispensing the heated solution and heating the carrier support or the like may be performed together.

Figure 7E:
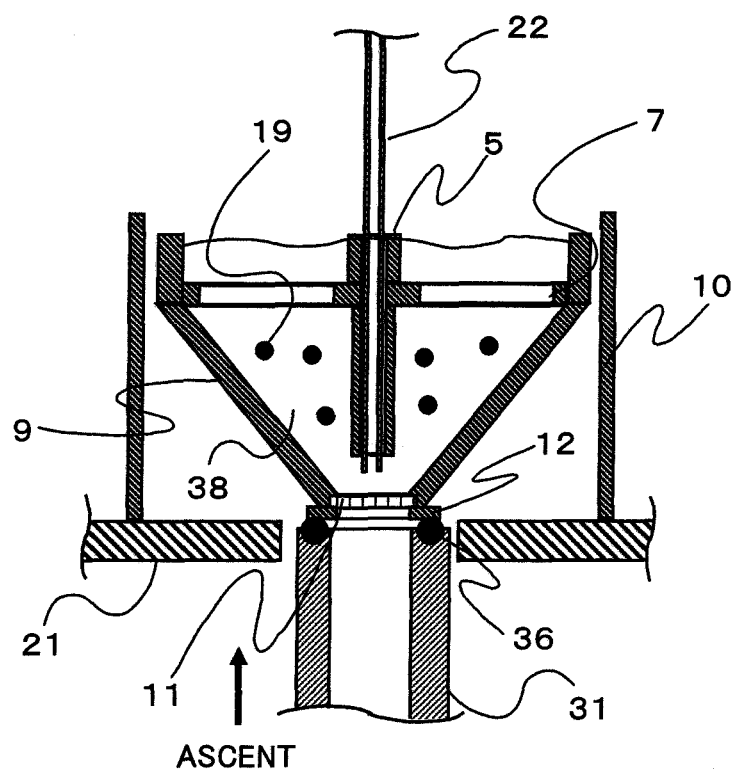
FIG. 7E is a diagram (5) illustrating the principle of operation of the carrier treating apparatus according to the second embodiment.
Figure 7F:
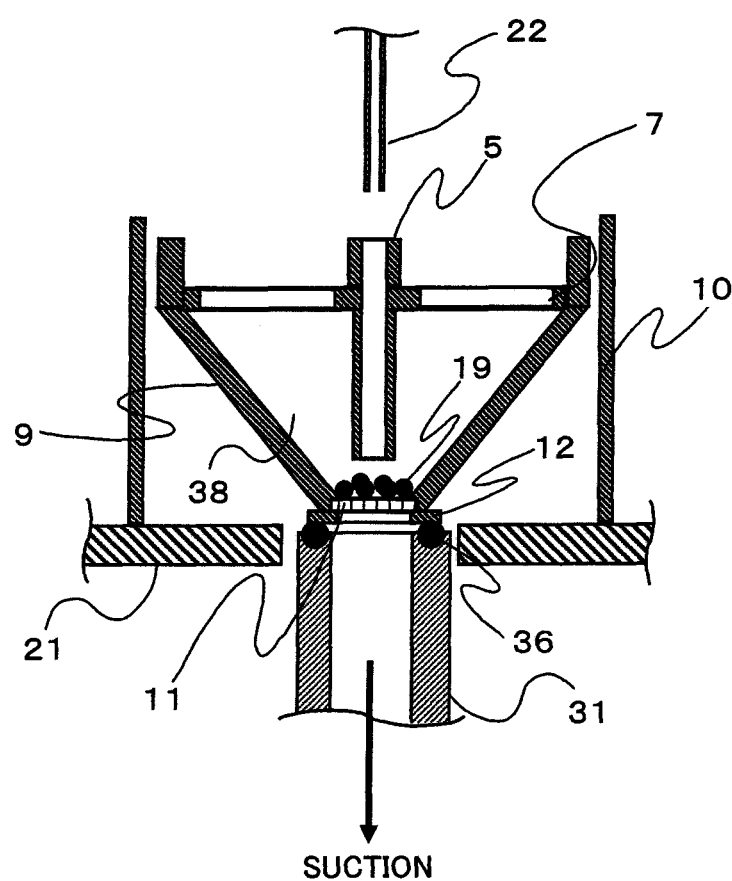
FIG. 7F is a diagram (6) illustrating the principle of operation of the carrier treating apparatus according to the second embodiment.

FIG. 7E illustrates a state immediately before suction start as the microbe-solution suction nozzle 31 is ascending and the donut-shaped holding plate 12 and an O ring 36 above the microbe-solution suction nozzle 31 are making close contact with each other. Such close contact may be made in any of the processes in FIGS. 7A to D. FIG. 7F illustrates a situation in which the suction pump 34 is activated, the mixed liquid 38 of the heated liquid and the polymer is discharged via the microbe collection filter 11, and the discharge is finished.

According to the processes of FIGS. 7A to E, the microbes 19 captured on the thermoplastic carrier 15 can be harvested on the microbe-collecting filter 11.

In the present embodiment, the supply of the heated solution 37 and the discharge of the mixed liquid 38 of the heated liquid and the polymer by suction are each performed once, but these processes may be repeated a plurality of times to harvest the microbes 19 on the microbe collection filter 11. Such a method of repeating a plurality of times can further liquefy and remove impurities on the microbe collection filter 11 and a solid residue of gelatin, which is the thermoplastic carrier 15 while heating them on the filter.

A feature of the carrier treating apparatus of the present invention is that the heated liquid 37 is supplied onto the microbe collection filter 11, thereby liquefying the thermoplastic carrier 15 from a position near the filter for filtration. In this manner, the temperature on the microbe collection filter 11 can be kept high, and furthermore, by dilution with the heated solution 37, the concentration of the thermoplastic polymer on the microbe collection filter 11 can be controlled to be low, the present invention is convenient as means for preventing clogging of the microbe collection filter 11.

Air flows 75 generated from suction by a collector 74 illustrated in FIG. 14 pass through the second through holes 4 and then through the gap 6, and are then exhausted via an air outlet of the collector 74. The microbes 19 going out of the air flows 75 are captured onto the surface of the thermoplastic carrier 15. At this time, a space between the upper lid 2 and the thermoplastic carrier 15 with respect to a diameter of the second through holes 4 is set at 1:1 or 1:2. With the space at the above ratio, the collection rate is further increased.

Other than the method of adding a heated solution from a lower portion of the thermoplastic carrier, as a sol-transition method, a method of adding the heated liquid 37 from above the thermoplastic carrier 15 of the microbe-collecting carrier cartridge 1 may be used. In this case, it is necessary to remove the upper lid 2.

Third Embodiment

Figure 8:
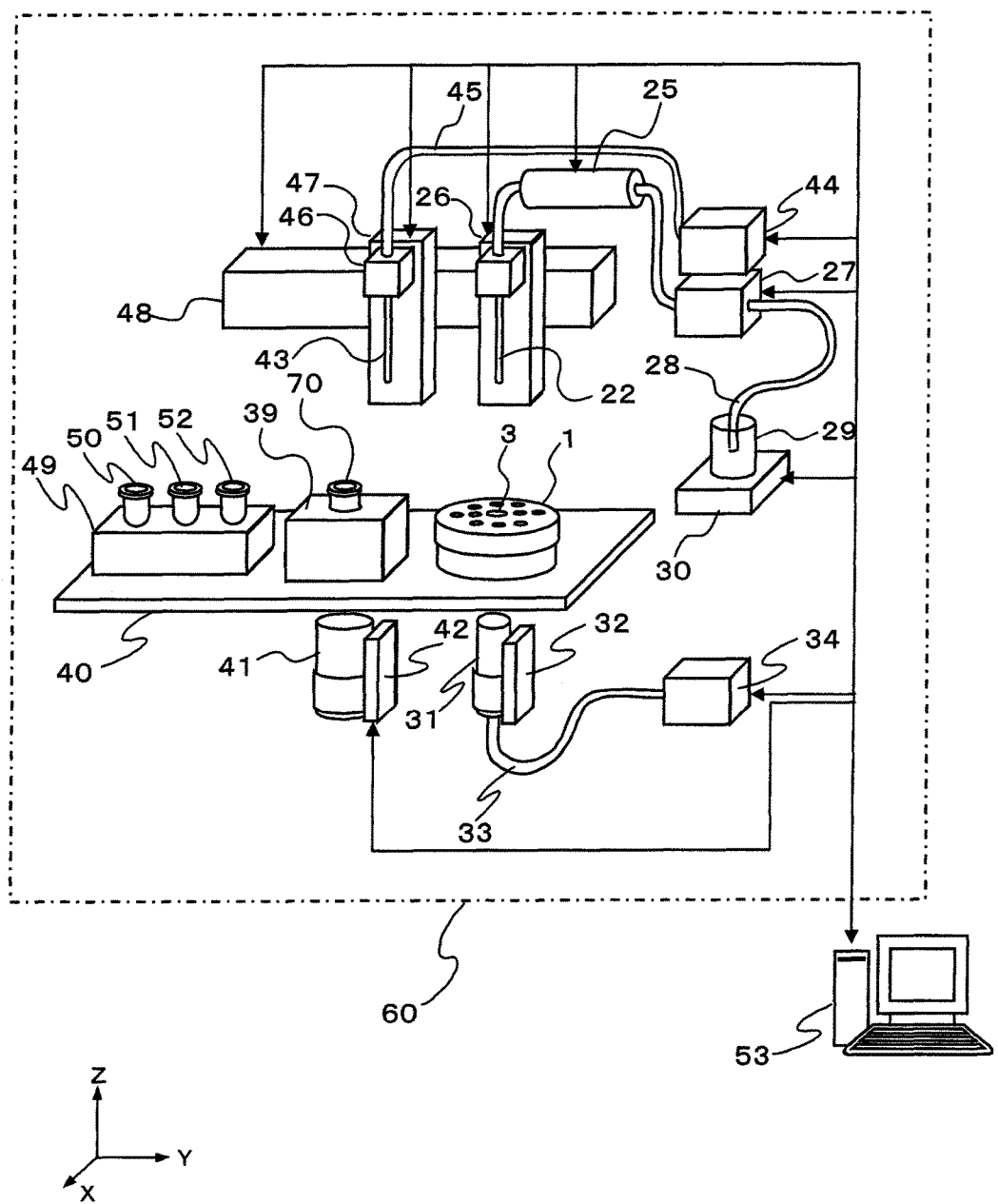
FIG. 8 is a diagram illustrating an outer appearance of an automatic microbe-count measuring device according to a third embodiment.

FIG. 8 is a schematic configuration diagram of an automatic microbe-count measuring device 60 in which a mechanism unit and a chemiluminescence measuring mechanism unit of the carrier treating apparatus according to the second embodiment are systemized. To the entire mechanism of the carrier treating apparatus of FIG. 6, a mechanism unit capable of automatically performing processes from ATP extraction to luminescence measurement on the microbes 19 is added, and the apparatus measures luminescence regarding the amount of ATP that is in proportion to the number of microbes 19 collected in the microbe-collecting carrier cartridge 1 and further calculates the number of microbes 19. The carrier process mechanism unit is as described in the second embodiment, and therefore is not described herein.

The chemiluminescence measuring mechanism unit will be described.

An ATP measurement container 70 is set up on a first container holder 39. The first container holder 39 is set up on a second plate member 40. A photodetector 41 can move in a z-axis direction by a third actuator 42. The ATP measurement container 70, the first container holder 39, and the photodetector 41 are aligned so that their centers are on the same axis in the z-axis direction. In general, as the photodetector 41, a Photomultiplier Tube (PMT) is suitably used in view of sensitivity. However, when the sensitivity as that of the PMT is not necessary, and if a reduction in device cost is weighed, a semiconductor element, such as a photodiode, may be used. In the specification, however, only the system of using a PMT or the like is described.

Shifts of the z-axis position by the third actuator 42 are used for controlling detection sensitivity. Since the light intensity is attenuated by the square of a distance from a light-emitting point, the sample container including a chemiluminescent substance is suitably close to a light-receiving surface. However, when a measurement target having a high ATP concentration is measured, it is also effective to put the detector away from the target to widen a detection limit, and the present automatic microbe-count measuring device makes that possible.

A liquid operating unit for use in a chemiluminescence measurement is formed of a second dispensing nozzle 43 to be a liquid exit when a liquid containing ATP is dispensed into the ATP measurement container 70, a second liquid-delivering pump 44, a fifth pipe 45 connecting the second dispensing nozzle 43, and a second nozzle holder 46 which fixes the second dispensing nozzle 43 and connects the second dispensing nozzle 43 and the fifth pipe 45. The second dispensing nozzle 43 can be positionally controlled by a fourth actuator 47 in the z-axis direction. Furthermore, the fourth actuator 47 and the third actuator as means of performing a carrier treatment are mounted on a fifth actuator, thereby controlling the position also in a y-axis direction.

On the second plate member 40, a tube setup holder 49 is set up where a plurality of sets (here, three sets) of solution tank tubes can be set up, and, to a first reagent tube 50, a second reagent tube 51, and a third reagent tube 52, an ATP elimination reagent, an ATP extraction reagent, and an ATP chemiluminescent reagent, etc. are introduced. These reagents are separated by using the second dispensing nozzle 43 to be dispensed into the microbe-collecting carrier cartridge 1 and the ATP measurement container 70.

The entire process of the automatic microbe-count measuring device 60 is continuously and automatically controlled by using a second control device 53.

Figure 9:
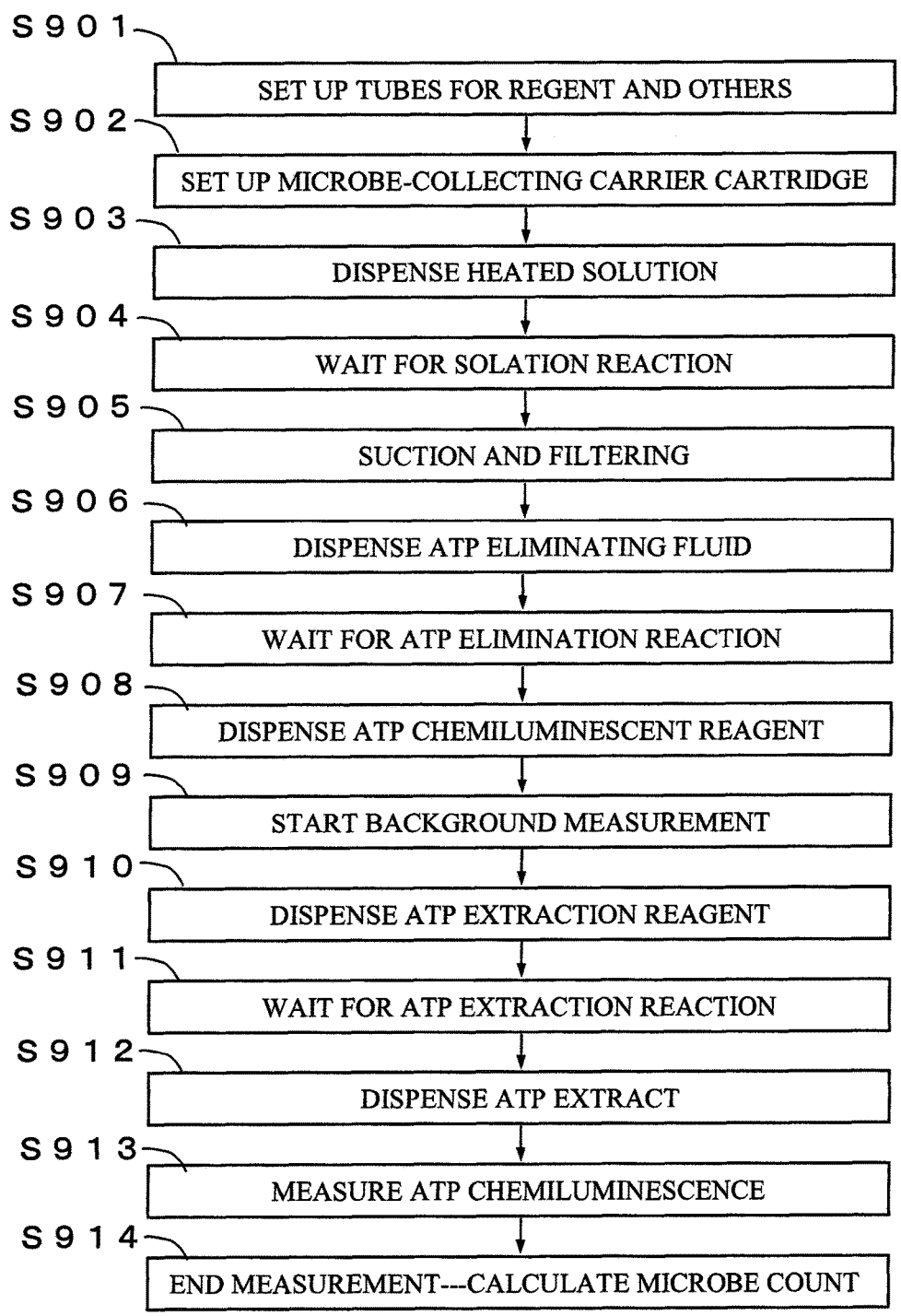
FIG. 9 is a flowchart for describing a procedure of measuring viable microbes by using the automatic microbe-count measuring device according to the third embodiment.
Figure 13A:
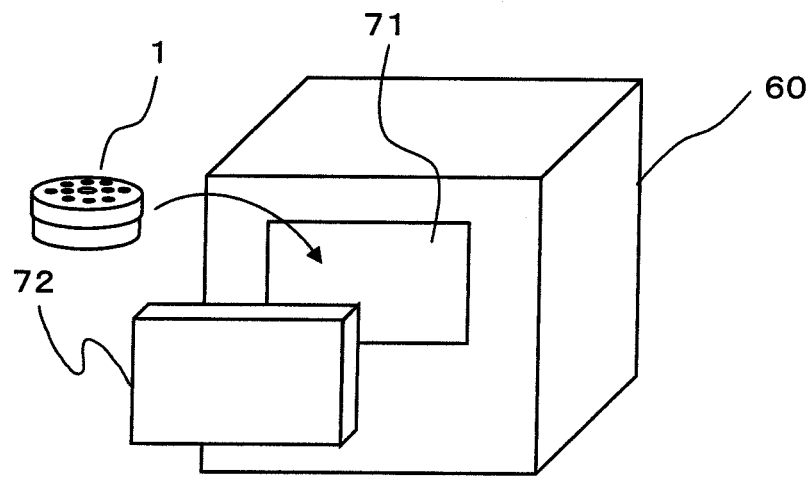
FIG. 13A is a schematic diagram (1) illustrating a state in which a collection carrier cartridge is being set up in the automatic microbe-count measuring device according to the third embodiment.
Figure 13B:
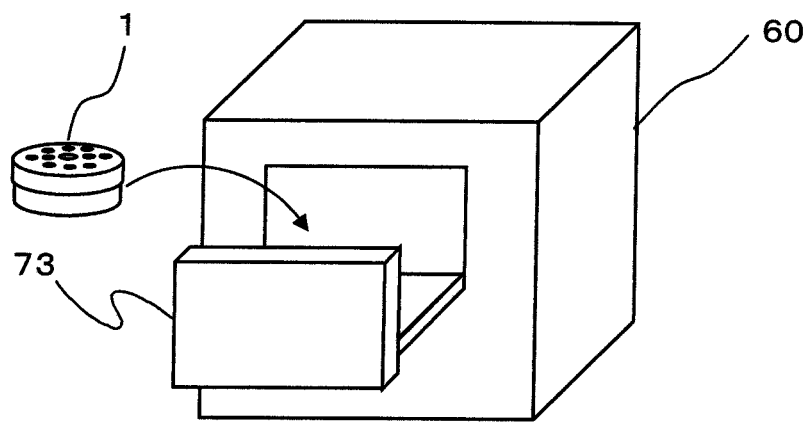
FIG. 13B is a schematic diagram (2) illustrating a state in which the collection carrier cartridge is being set up in the automatic microbe-count measuring device according to the third embodiment.

With reference to FIG. 9, the procedure of an automatic microbe counting method using FIG. 8 will be described. First, the ATP measurement container 70, the first reagent tube 50 containing the ATP elimination reagent, the second reagent tube 51 containing the ATP extraction reagent, and the third reagent tube 52 containing the ATP chemiluminescent reagent are set up in the tube setup holder 49 (S901). Next, the microbe-collecting carrier cartridge 1 is mounted on a collector for collecting airborne microbes, and the microbe-collecting carrier cartridge 1 collecting the microbes 19, the microbe-collecting carrier cartridge 1 harvesting falling microbes, or the microbe-collecting carrier cartridge 1 gathering adherent microbes is set up on the second plate member 40 (S902). The inside of the automatic microbe-count measuring device 60 is a light-shielding housing (chassis) for chemiluminescence measurement. The setup processes of the above steps S901 and S902 are performed via a window 71 attached to the device with its light-shielding door 72 removed therefrom. Alternatively, the setup processes are performed by using a drawer 73 allowing the second plate member 40 to be withdrawn (FIG. 13).

The inside of the device is light-shielded in a closed state.

In response to an instruction of starting the process given from the second control device 35, the first dispensing nozzle 22 is first moved immediately above the microbe collection filter 11 in the liquid storage container 9 of the microbe-collecting carrier cartridge 1 to dispense the heated solution 37 supplied from the first solution tank 29 (S903). The dispensing amount can be arbitrarily set. After the end of dispensing, after a lapse of a wait time for liquefaction reaction of the thermoplastic carrier 15 (S904), the mixed liquid 38 of the heated liquid and the polymer is sucked for filtration via the microbe collection filter 11 by the microbe-solution suction nozzle 31 (S905). Upon the end of the processes from S903 to 905, the microbes 19 are harvested on the microbe-collecting filter 11.

Next, the procedure goes to a step of measuring the amount of ATP in the viable microbes. From the first reagent tube 50, the ATP elimination reagent is separated by the second dispensing nozzle 43, and the separated ATP elimination reagent is dispensed onto the microbe collection filter 11 (S906). After 30 minutes of a wait time for ATP elimination reaction (S907), the ATP extraction reagent is separated from the second reagent tube 51 by the second dispensing nozzle 43, and the separated ATP extraction reagent is dispensed on the microbe collection filter 11 (S910) to extract ATPs from the microbes. Note that, before the procedure enters the process of S909, the ATP chemiluminescent reagent is separated from the third reagent tube 52 by the second dispensing nozzle 43, the separated ATP chemiluminescent reagent is dispensed into the ATP measurement container 70 (S908), and a background measurement on the chemiluminescent reagent is started (S909). After 30 seconds to one minute, which are wait time for ATP extraction reaction (S911), the second dispensing nozzle 43 is introduced into the liquid tank container 9 of the microbe-collecting carrier cartridge 1 to separate the ATP extraction reagent reacted with the microbe 19, the separated ATP extraction reagent is dispensed into the ATP measurement container 70 (S912), and biochemical luminescence of the ATP is measured (S913). From measured ATP luminescence intensity, the microbe count is calculated (S914).

Figure 10:
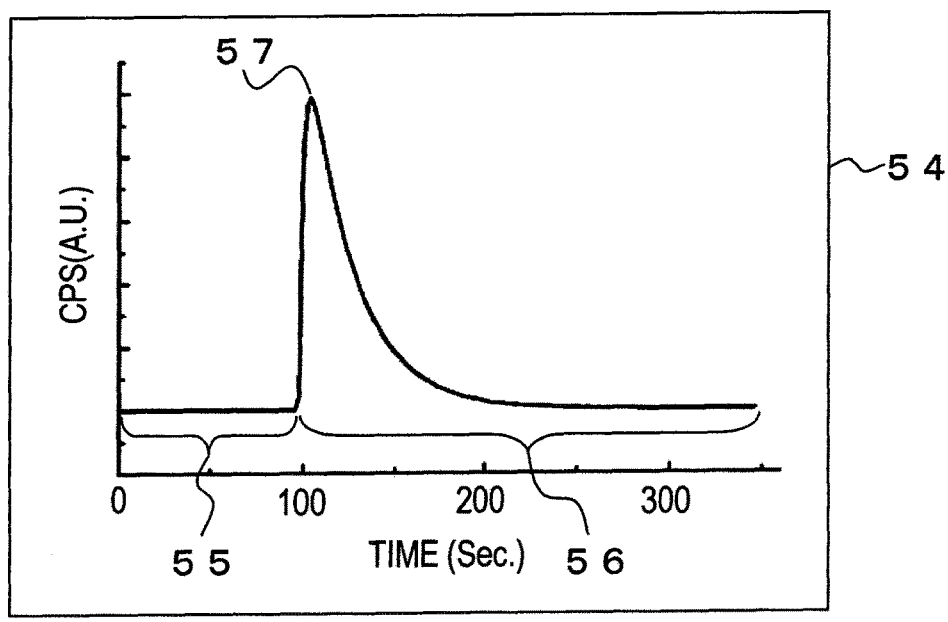
FIG. 10 is a diagram illustrating an ATP chemiluminescence curve with respect to elapsed time obtained by the automatic microbe-count measuring device according to the third embodiment.

FIG. 10 illustrates a typical example of an ATP-chemiluminescence chronological curve graph 54 represented with measuring time on the horizontal axis and a number of photons per unit second (Count Per Second: CPS) on the vertical axis. This example is that, after obtaining a background signal 55 before dispensing a chemiluminescent reagent for 100 seconds, an ATP chemiluminescence signal 56 is obtained for 250 seconds after 100 seconds. Here, a flash-type (highly-sensitive-type) chemiluminescent reagent exhibiting a peak value 57 in signal intensity in several seconds immediately after the chemiluminescent reagent is dispensed is used.

Figure 11:
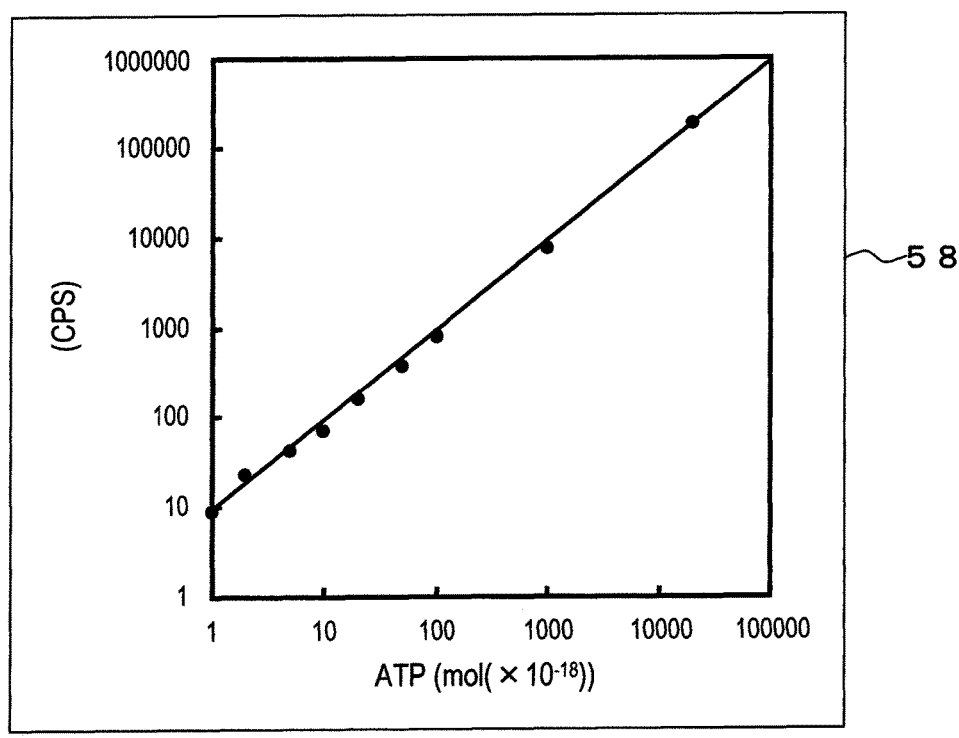
FIG. 11 is a graph illustrating a relation between an ATP concentration and chemiluminescence intensity obtained by the automatic microbe-count measuring device according to the third embodiment.

To calculate a microbe count, data management is required as for a relation between the luminescence intensity of the photodetector 41 and the number of ATP molecules by creating a standard (calibration) line in advance. FIG. 11 is a standard-line graph 58 obtained by converting a difference obtained by subtracting a value of the background signal 55 from the peak value 57 of FIG. 10 into a numerical form and plotting the result to each concentration. The standard line obtained is in a linear form from an extremely low concentration of 1 amol to 100000 amol, that is, representing a quantitative intensity change.

From this standard-line graph 58, the microbe count can be calculated for automatic output of data (S911). This can be calculated since the amount of ATP contained is determined depending on the microbes. For example, the amount is 17 amol/microbe for *Bacillus subtilis*, 1.52 amol/microbe for *Staphylococcus aureus*, and 1 to 2 amol/microbe for *Escherichia coli*.

Figure 12:
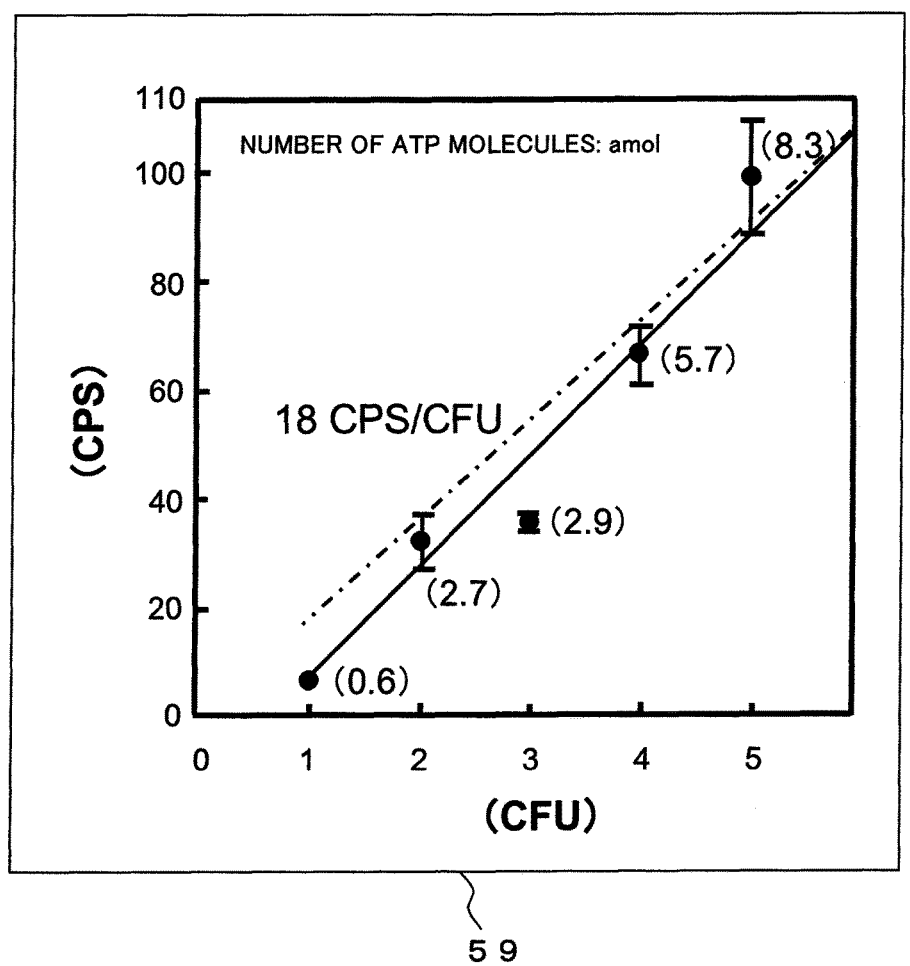
FIG. 12 is a microbe-count dependency graph of a microbe count on the horizontal axis and chemiluminescence intensity on the vertical axis measured by the automatic microbe-count measuring device according to the third embodiment.

FIG. 12 illustrates results of checking detection sensitivity and detection accuracy in *Escherichia coli* by using a suspension, as a model sample, obtained by dilution of standard strains (10,000 cfu of Easy QA Ball *Escherichia coli* from Nissui Pharmaceutical Co., Ltd.) with purified water. A suspension is spot-applied onto a thermoplastic carrier 15 of the microbe-collecting carrier cartridge 1 to change the amount of spot application, thereby controlling the microbe count, and a microbe-count dependency graph of luminescence intensity 59 is illustrated with the microbe count plotted on the horizontal axis and luminescence intensity plotted on the vertical axis.

The amounts of ATP per 1 CFU of 1 to 5 CFU were 0.6, 2.7, 2.9, 5.7, and 8.3 (ATP: 12 CPS/amol). That is, the average was 1.2 amol per 1 CFU. A catalog value of the standard strain is 1.5 amol/CFU, and a broken line of FIG. 12 is an ideal standard line when created based on the catalog value. The experiment results match with the values of the ideal standard line, indicating that a measurement can be performed with high reliability and accuracy. It is also indicated that the device is a highly-sensitive device capable of measurement from 1 CFU.

1 . . . microbe-collecting carrier cartridge; 2 . . . upper lid; 3 . . . first through hole; 4 . . . second through hole; 5 . . . dispensing nozzle guide; 6 . . . gap; 7 . . . carrier support base; 8 . . . third through hole; 9 . . . liquid storage container; 10 . . . outer cylinder; 11 . . . microbe-collection filter; 12 . . . donut-shape stopper plate; 13 . . . fourth through hole; 14 . . . fifth through hole; 15 . . . thermoplastic carrier; 17 . . . support portion; 18 . . . mesh; 19 . . . microbe; 20 . . . dust; 21 . . . first plate member; 22 . . . first dispensing nozzle; 23 . . . first nozzle holder; 24 . . . first pipe; 25 . . . pipe heating heater; 26 . . . second pipe; 27 . . . first liquid-delivering pump; 28 . . . third pipe; 29 . . . first solution tank; 30 . . . solution tank heater; 31 . . . microbe-solution suction nozzle; 32 . . . second actuator; 33 . . . fourth pipe; 34 . . . suction pump; 35 . . . first control; 36 . . . first control device; 37 . . . heated solution; 38 . . . mixed liquid of heated liquid: 39 . . . first container holder; 40 . . . second plate member; 41 . . . optical detector; 42 . . . third actuator; 43 . . . second dispensing nozzle; 44 . . . second liquid-delivering pump; 45 . . . fifth pipe; 46 . . . second nozzle holder; 47 . . . fourth actuator; 49 . . . tube setup holder; 50 . . . first reagent tube; 51 . . . second reagent tube; 52 . . . third reagent tube; 53 . . . second control device; 54 . . . ATP-chemiluminescence chronological curve graph; 55 . . . background signal; 56 . . . ATP chemiluminescence signal; 57 . . . peak value; 58 . . . standard line graph; 59 . . . a microbe-count dependency graph of luminescence intensity; 60 . . . automatic microbe-count measuring device; 70 . . . ATP measurement container; 71 . . . window; 72 . . . light-shielding door; 73 . . . drawer; 74 . . . collector; and 75 . . . air flow

What is claimed is:

1. A carrier cartridge comprising:
a thermoplastic carrier for collecting one or more microbe, the thermoplastic carrier including a gel-sol transition polymer which is turned into a sol state at a temperature equal to or higher than 30° C.;
a support base supporting the thermoplastic carrier and having a first opening penetrating the support base; and
a container having an inverted-cone shape, the inverted-cone shape having an upper portion wider than a lower portion, the support base being supported by the upper portion and inside of the container, and the container disposed to cover the first opening and having a filter being at the lower portion of the inverted-cone shape, and the container and filter configured to filter the solated thermoplastic carrier including the one or more microbe within the container via the filter when the gel-sol transition polymer is turned into a sol state at the temperature equal to or higher than 30° C.,
wherein the thermoplastic carrier has a second opening penetrating the thermoplastic carrier,
wherein each of the first opening and the second opening are arranged coaxially,
wherein a projected area of the support base is wider than a projected area of the filter, and
wherein a solution is supplied from the first opening through the second opening to the filter at the lower portion of the inverted-cone shape,
wherein the support base has a plurality of through holes penetrating the support base and configured to pass the carrier polymer in a sol state through the plurality of the through holes to the filter at the lower portion of the inverted-cone shape.

2. The carrier cartridge according to claim 1, wherein the thermoplastic carrier is gelatin.

3. The carrier cartridge according to claim 1, wherein the thermoplastic carrier is gelatin containing an alcohol content.

4. The carrier cartridge according to claim 3, wherein the alcohol content of the thermoplastic carrier is glycerol.

5. The carrier cartridge according to claim 1, wherein the thermoplastic carrier is in a plate shape in a gel state.

6. The carrier cartridge according to claim 1, wherein the support base further comprises at least one through hole located at a center of a protrusion which extends from a flat plate of the support base.

7. The carrier cartridge according to claim 6, wherein the protrusion of the support base has a same center axis as a center axis of the through hole of the thermoplastic carrier, and the thermoplastic carrier wraps around the protrusion and is supported by the support base.

8. The carrier cartridge according to claim 1, wherein at least one piece of the filter is attached to the container, and the container has a plate part having a donut shape for attaching the filter to the container.

9. The carrier cartridge according to claim 1, wherein the container is provided inside an outer cylinder, and has a gap between the outer cylinder and a liquid holding part of the container.

10. The carrier cartridge according to claim 1, wherein the filter is a membrane filter of HEPA (High Efficiency Particulate Air) or porous membrane filter which does not let a substance larger than or equal to 0.45 microns pass through.

11. The carrier cartridge according to claim 1, further comprising a lid member covering the thermoplastic carrier, the lid member being arranged to face the container via the thermoplastic carrier, and having a plurality of through holes.

12. The carrier cartridge according to claim 11, wherein at least one of the through holes of the lid member has a positional relation of passing through a center axis of a protrusion of the support base and a center axis of the opening of the thermoplastic carrier.

13. The carrier cartridge according to claim 1, wherein the container having an inverted-cone shape further comprises an upper opening and a lower opening positioned below and narrower than the upper opening, and wherein the support base supporting the thermoplastic carrier is positioned at the upper opening and the filter is positioned below the support base at the lower opening.

14. The carrier cartridge according to claim 13, wherein the container is provided inside an outer cylinder, and has a gap between the outer cylinder and a liquid holding part of the container, the gap configured to provide an intake for the inflow of air bypassing the filter.

15. The carrier cartridge according to claim 1, wherein the thermoplastic carrier is a solid polymer.

* * * * *